US012121749B2

(12) United States Patent
Zhao et al.

(10) Patent No.: US 12,121,749 B2
(45) Date of Patent: Oct. 22, 2024

(54) IMAGE DEFORMATION METHODS AND CURVED COUCH FOR RADIOTHERAPY TREATMENT PLANNING

(71) Applicants: Tianyu Zhao, St. Louis, MO (US); Sasa Mutic, St. Louis, MO (US)

(72) Inventors: Tianyu Zhao, St. Louis, MO (US); Sasa Mutic, St. Louis, MO (US)

(73) Assignee: Washington University, St. Louis, MO (US)

( * ) Notice: Subject to any disclaimer, the term of this patent is extended or adjusted under 35 U.S.C. 154(b) by 813 days.

(21) Appl. No.: 17/283,870

(22) PCT Filed: Oct. 10, 2019

(86) PCT No.: PCT/US2019/055709
§ 371 (c)(1),
(2) Date: Apr. 8, 2021

(87) PCT Pub. No.: WO2020/077142
PCT Pub. Date: Apr. 16, 2020

(65) Prior Publication Data
US 2021/0346720 A1  Nov. 11, 2021

Related U.S. Application Data

(60) Provisional application No. 62/743,953, filed on Oct. 10, 2018.

(51) Int. Cl.
*A61N 5/10*  (2006.01)
(52) U.S. Cl.
CPC .................. *A61N 5/1039* (2013.01)
(58) Field of Classification Search
CPC ........ A61N 5/10; A61N 5/1039; A61N 5/103; A61N 2005/1097; A61B 5/0036;
(Continued)

(56) References Cited

U.S. PATENT DOCUMENTS 7,017,209 B1  3/2006  De Jong et al.
7,173,265 B2  2/2007  Miller et al.
(Continued)

FOREIGN PATENT DOCUMENTS

WO  2018048507 A1  3/2018
WO  2020077142 A1  4/2020

OTHER PUBLICATIONS

International Search Report and Written Opinion dated Feb. 11, 2020 from related Patent Application No. PCT/US2019/055709; 14 pgs.

*Primary Examiner* — Jurie Yun
(74) *Attorney, Agent, or Firm* — Polsinelli PC

(57) ABSTRACT

Disclosed herein is a method for deforming patient images obtained with a couch of one set of physical properties (e.g. curvature) based on the physical properties (e.g. curvature) of a couch where radiation therapy treatment will be performed. Also disclosed herein is a radiotherapy delivery system which includes a non-flat couch top, on-couch planning, and optional deformable image registration. The methods and systems use images from scanners of various couch top shapes for treatment of radiotherapy patients without a need for specialized treatment planning imaging. In such methods and systems, treatment delivery can be performed based on only diagnostic images and setup images acquired at the time of treatment on the treatment machine. The radiotherapy delivery systems can include any combination of volumetric imaging with radiotherapy treatments with photon, proton, electron, and\or other particle radiation.

20 Claims, 14 Drawing Sheets

(58) Field of Classification Search
CPC ......... A61B 5/055; A61B 5/704; A61B 6/032; A61B 6/5235; A61B 6/5247; A61B 6/12; A61B 8/5261; A61B 8/4416; G06T 3/18
See application file for complete search history.

(56) References Cited

U.S. PATENT DOCUMENTS

| | | |
|---|---|---|
| 9,757,588 B2 | 9/2017 | Kaus et al. |
| 2005/0251029 A1 | 11/2005 | Khamene et al. |
| 2006/0020195 A1 | 1/2006 | Falco et al. |
| 2009/0087124 A1 | 4/2009 | Nord et al. |
| 2011/0019889 A1 | 1/2011 | Gering et al. |
| 2012/0043475 A1 | 2/2012 | Ahn |
| 2012/0167898 A1 | 7/2012 | Buchsbaum et al. |
| 2013/0217948 A1 | 8/2013 | Mihaylov |
| 2013/0289332 A1 | 10/2013 | Purdie et al. |
| 2014/0323851 A1 | 10/2014 | Barberi et al. |
| 2015/0360054 A1 | 12/2015 | Jeong |
| 2016/0310761 A1 | 10/2016 | Li et al. |

IMAGE DEFORMATION METHODS AND CURVED COUCH FOR RADIOTHERAPY TREATMENT PLANNING

CROSS REFERENCE TO RELATED APPLICATIONS

This application claims the benefit of International Patent Application No. PCT/US2019/055709, filed Oct. 10, 2019, which claims priority to U.S. Provisional Application No. 62/743,953, filed Oct. 10, 2018, the contents of which are entirely incorporated by reference herein.

FIELD OF THE INVENTION

The present disclosure is related to processes for deforming diagnostic images based on the radiotherapy equipment to be used and any desired patient positioning for radiotherapy treatment.

BACKGROUND OF THE INVENTION

Since the earliest days of radiotherapy machines, radiotherapy couches (tabletops) have been flat. The couches may be flat to position a patient for a radiotherapy treatment, as a patient often needs to be moved and moving a patient on a flat couch is easy and controllable. It is worth noting that if the whole couch top is moved to reposition the patient, the flat shape of the couch is then less important. However, since so many of the treatments in early days of radiotherapy relied on some form of patient repositioning on the couch, rather than moving of the couch, it was likely necessary to have flat couch tops. Radiotherapy techniques in the early days also relied on simple beam arrangements with many treatments having only one to four beams and generally involving radiation beams of lower energies. Radiation beams traversing the couch are less attenuated if a "tennis racquet" like feature is employed within the treatment couch and many of the older treatment machines had such feature. With a tennis racquet insert, a radiation beam is mainly passing through air and beams entering the patient through the tennis racquet part of the couch would be less attenuated and would deliver less radiation to the patient's skin as well. Imbedding a tennis racquet into a couch is really only practical if the couch is flat. Through the years, radiotherapy techniques evolved to include many more beams and this was especially accelerated with intensity modulated radiation therapy (IMRT) where typically seven or more radiation beams are involved and very commonly an arc based delivery is used. Over time, higher beam energies were also adopted and attenuation in the couch became less important. Another development was introduction of carbon fiber based couches where radiation traversing such couch is much less attenuated than couches made of plastics and other composite materials. Other more radiolucent materials similar to carbon fiber are available. With multi-beam delivery, higher beam energies, and use of carbon fiber, couches evolved to not having the tennis racquet feature and mainly being monolithic flat surfaces. Notches were imbedded in some couches which allow precise registration\coupling with patient immobilization. These notches and registration of patients to the treatment couch enable couches to be positioned in almost the same position for each fraction of patient's treatment. Precise couch positioning led to automated couch positioning and electronic tracking of couch positions between treatment fractions. Image guided radiation therapy (IGRT) further advanced to automation of couch motions and robotic control of some couches. Despite these advancements, the fundamental flat shape of the treatment couch has not changed. As such, radiotherapy couches are completely flat today, regardless of other advances in radiotherapy which could take advantage of non-flat couches.

Imaging in diagnostic radiology is typically performed on computed tomography (CT), magnetic resonance imaging (MRI), positron emission tomography (PET), and/or single photon emission computed tomography (SPECT) scanners, all typically equipped with non-flat (curved) couch tops. These devices use non-flat couch tops because curved couches are more compatible with their ring shape and non-flat couches also increase the use of the available area of the imaging field of view (FOV). Since the diagnostic images are acquired on couches with non-flat tops and radiotherapy delivery is performed with flat couches, radiotherapy treatment planning has historically required special treatment planning images acquired on patient imaging devices equipped with flat couches. Such scanners are typically called radiotherapy simulators and patients would undergo a radiotherapy simulation between diagnostic imaging and the actual treatment delivery which inevitably always delays the treatment and introduces additional medical procedures, costs, and risk to patients.

Overall it is desirable to bypass the radiotherapy simulation and enable a method where the number of steps between diagnosis and treatment are as few as possible. Therefore, there is a need for systems and methods for synergizing the diagnostic images and treatment planning for radiotherapy.

SUMMARY OF THE INVENTION

In an embodiment, diagnostic images are deformed\morphed based on the consideration of treatment radiotherapy equipment with or without consideration for desired patient positioning. In one embodiment, the deformation\morphing of images can be based on the shape of the radiotherapy couch top. The deformed\morphed images place patient diagnostic images in a position closer to the actual radiotherapy treatment position to increase clinician's confidence that a simulation scan can be bypassed and patient can proceed directly to radiotherapy treatment based on deformed\morphed diagnostic images and with treatment plans based on those images. The treatment plans include calculation of radiation dose distributions on deformed\morphed images as well as decisions\plans made by healthcare providers (e.g. physicians) during patient treatment course. Such decisions\plans can be made in tumor boards, multidisciplinary clinics, patient consultations, etc. The treatment plan created based on deformed\morphed diagnostic images could be used as is on the first day of treatment or could be modified (adapted) based on the images acquired in the treatment room. Combining a decision to treat based on a plan created on deformed\morphed diagnostic images and creating a brand new plan based on the images acquired in the treatment room at the time of treatment is considered an equivalent process. It is important to note that the deformation/morphing based on the consideration of treatment radiotherapy equipment with or without consideration for desired patient positioning creates images with changes in anatomy based on the shape of the patient support structure. This is distinctly different from deforming a patient image based on another image of the same patient. In an embodiment where diagnostic images are deformed\morphed based on the consideration of treatment radiotherapy equipment with or without consideration for desired patient positioning, reference patient anatomy from another image does not exist and the images are deformed/morphed based on the shape of patient support on the radiotherapy equipment, therefore creating a new set of images.

Provided herein is a streamlined radiotherapy process based on deformed\morphed diagnostic images as illustrated in FIG. 1A. The proposed process is not affected by variations in the imaging equipment (scanners and couch geometries) and modalities (e.g. CT or MRI) and patient positioning as deformation\morphing can account for changes in patient position as well. For example, the deformation\morphing could be used to change position of patient's extremities.

The method and system may enable treatment planning and treatment decision during the initial consultation, tumor board, or during other decision points. The method and system may enable more informed communication among multidisciplinary physicians and with the patient. A successful implementation of such method and system may increase the number of eligible patients receiving radiotherapy while improving identification of ineligible patients at early stages of the treatment process.

The method and system may enable the treatment plan based on deformation\morphing of images based on the geometry of the treatment machine to be adapted on the first fraction of the patient's treatment with modern planning and imaging technique.

One embodiment includes a radiotherapy delivery system which includes a volumetric imaging capability, a non-flat couch top, and a radiotherapy treatment planning software capable of treatment planning and dose calculation with volumetric images obtained on the delivery system. Such system would allow use of treatment plans created with volumetric images based on the same or similar shape couch top for guidance of treatment. Similar shape couch tops would have curvature which does not change patient body position by more than a few centimeters.

Another embodiment includes a radiotherapy delivery system which includes a volumetric imaging capability, a non-flat couch top, and a radiotherapy treatment planning software capable of treatment planning and dose calculation with volumetric images obtained on the system and a deformable image registration capability. Such system would allow use of treatment plans created with volumetric images based on the same shape couch top or a different shape couch top for guidance of treatment. The different shape couch tops could change patient body position by more than a few centimeters. It is important to note that in such embodiments, the deformable image registration means that one image is deformed to match the shape of another image, which is different than deforming/morphing images based on couch shape. In such embodiments, the images obtained on the treatment machine may be deformed to match images obtained during diagnosis or patient cancer care planning. Images obtained during diagnosis or patient cancer care planning may also be deformed to match the images obtained on the treatment machine. Alternatively, the patient anatomy contours based on images obtained on the treatment machine may be deformed based on images obtained during diagnosis or patient cancer care planning. Patient anatomy contours based on images obtained during diagnosis or patient cancer care planning may also be deformed based on the images obtained on the treatment machine. Yet another alternative is for radiation dose distributions created based on images obtained on the treatment machine may be deformed based on images obtained during diagnosis or patient cancer care planning. Radiation dose distributions created based on images obtained during diagnosis or patient cancer care planning may also be deformed based on the images obtained on the treatment machine.

Yet another embodiment includes a radiotherapy delivery system which includes a volumetric imaging capability, a non-flat couch top, and a radiotherapy treatment planning software capable of deformable image registration. Such system would allow use of treatment plans created with volumetric images based on the same shape couch top or a different shape couch top for guidance of treatment. The different shape couch tops could change patient body position by more than a few centimeters. It is important to note that in such embodiments, the deformable image registration means that one image is deformed to match the shape of another image, which is different than deforming/morphing images based on couch shape. In such embodiments, the images obtained on the treatment machine may be deformed to match images obtained during diagnosis or patient cancer care planning. Images obtained during diagnosis or patient cancer care planning may also be deformed to match the images obtained on the treatment machine. Alternatively, the patient anatomy contours based on images obtained on the treatment machine may be deformed based on images obtained during diagnosis or patient cancer care planning. Patient anatomy contours based on images obtained during diagnosis or patient cancer care planning may also be deformed based on the images obtained on the treatment machine. It is important to note that the treatment planning software may also be known as control console software, image registration software, or by other names all representing the same software which consumes images acquired on the treatment system and processes them in order to provide instructions to the system on what settings should be used for patient treatment.

BRIEF DESCRIPTION OF THE DRAWINGS

The description will be more fully understood with reference to the following figures and data graphs, which are presented as variations of the disclosure and should not be construed as a complete recitation of the scope of the disclosure, wherein.

DETAILED DESCRIPTION

Figure 1A:
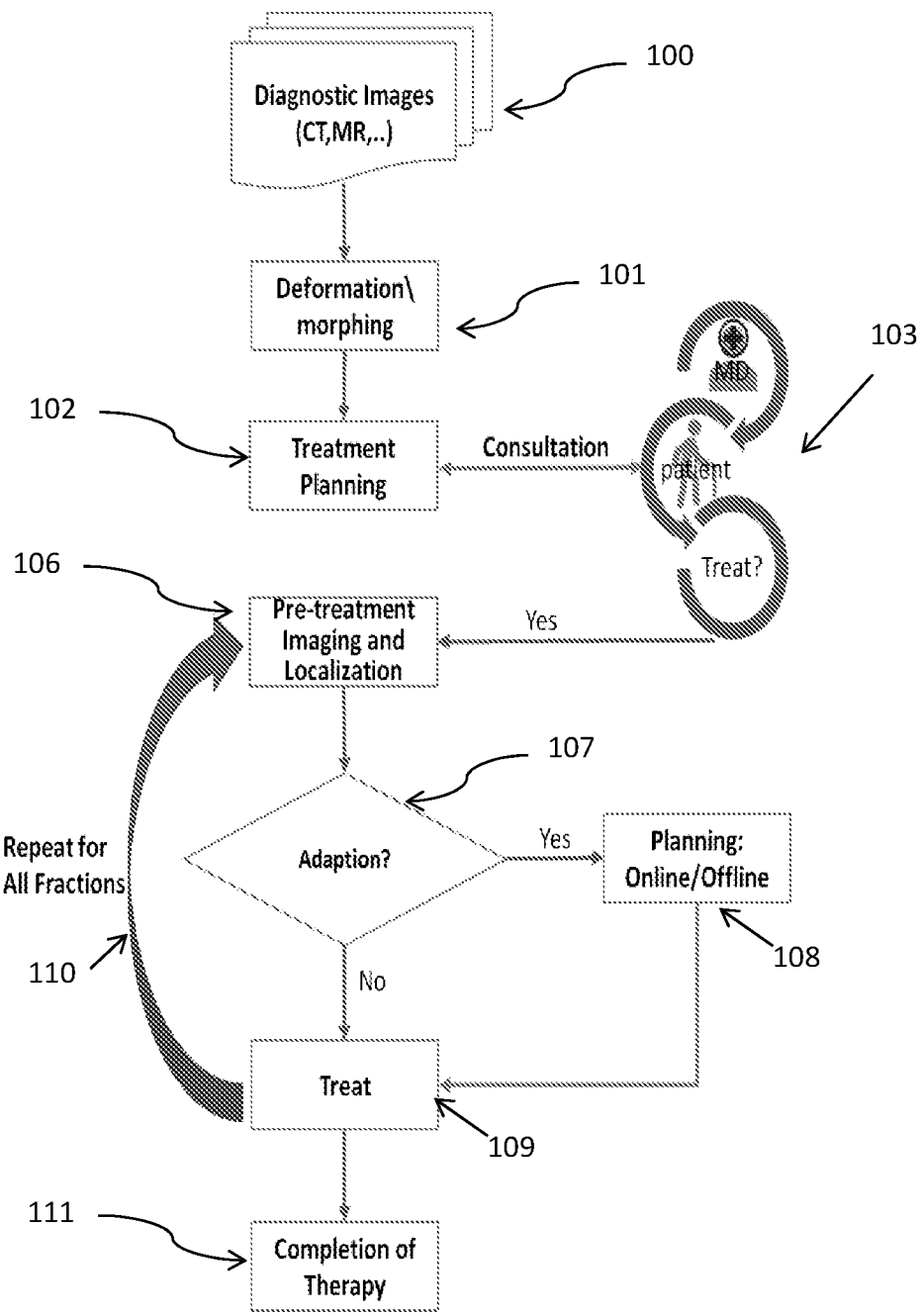
FIG. 1A shows a radiotherapy method based on morphed/deformed diagnostic, staging, work-up, etc. images based on the physical properties (e.g. curvature) of the treatment machine couch.

The disclosure may be understood by reference to the following detailed description, taken in conjunction with the drawings as described below. It is noted that, for purposes of illustrative clarity, certain elements in various drawings may not be drawn to scale.

Reference to "one embodiment", "an embodiment", or "some embodiments" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others.

As used herein, the terms "deform", "deformation", "morph" refer to adjusting an image based on the shape of the couch the patient was on when acquiring the image. These terms do not include adjusting an image based on the shape of a second image.

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms.

Provided herein are methods of radiotherapy treatment planning by deforming images based on treatment couch shape. In various embodiments, a radiotherapy treatment plan may include diagnostic images, deformed diagnostic images, radiation dosage calculations, tumor boards, multi-disciplinary clinics, patient consultations, or combinations thereof. The treatment plans may include a calculation of radiation dose distributions on deformed\morphed images as well as decisions\plans made by healthcare providers (e.g. physicians) during patient treatment course. Such decisions\plans can be made in tumor boards, multidisciplinary clinics, patient consultations, etc. The treatment plan may be used to define the calculation of radiation dose distributions on patient images. The calculation can be of doses that are to be delivered or recreation of doses that have been delivered. However, the treatment plan may also include other decisions by healthcare providers (e.g. physicians) on how to manage the treatment and treatment details of a radiotherapy patient and may not always require dose distributions. Healthcare providers (e.g. physicians) can make decisions about patient treatments without dose distributions and based on images alone. The treatment plan created based on deformed\morphed diagnostic images may be used as is on the first day of treatment or may be modified (adapted) based on the images acquired in the treatment room. Combining a decision to treat based on a plan created on deformed\morphed diagnostic images and creating a brand new plan based on the images acquired in the treatment room at the time of treatment is considered an equivalent process.

Modern image deformation/morphing techniques enable deformation of images based on specific landmarks. In an embodiment, patient diagnostic images used for diagnosis/staging/work up of a patient may be deformed based on the physical properties (e.g. curvature) of a couch where subsequent medical procedures (e.g. radiation therapy treatment) will be performed. In this embodiment, the radiotherapy simulation could then be bypassed and patient images acquired outside radiation therapy department could be used for treatment planning.

Further provided herein are radiotherapy delivery systems with non-flat couch tops. In an embodiment, curved couches may be used with radiotherapy machines. Over the past 20 to 30 years, radiotherapy has seen many developments which would make use of curved couches with treatment delivery machines desirable. Despite this, flat couches have remained standard on present radiotherapy machines. Most radiotherapy linear accelerators today are equipped with cone beam computed tomography (CBCT) capability. A curved couch would lend itself to increased clearance for CBCT scanning and increased usable scan field of view (FOV). Even with linacs coupled with MRI or PET, curved couches would be beneficial. Similarly, many treatment techniques have arc based treatment capabilities (e.g. volumetric modulated arc therapy (VMAT)) and curved couch would again offer increased clearance and reduced likelihood of collision. The cradle shape of curved couches uses gravity to position the patient in the center of the table and reduce inter-fractional variability in patient positioning. Flat couches do not offer a natural reference on how patient should be centered on the couch. Curved couches are also generally less wide than flat couches and as such should offer increased clearance for conventional treatments and would increase the ability to place a radiation beam closer to the patient when close proximity between the machine and patient is needed (e.g. particle beam therapy). Many modern radiotherapy systems are ring shape and curved couches increase the usable space of the ring (gantry) opening, improve the usable space of the FOV, and again lend themselves to arc based treatments. Another example where curved couch would be more advantageous is use of robotic couches. With robotic radiotherapy couches, the couch is used to robotically reposition the patient from millimeters with some models to meters with other models. In either case, the cradling shape of the couch top would offer increased patient stability and positional safety compared to a flat couch.

However, the adoption of non-flat couch tops in radiotherapy is not universally needed and there are procedures which benefit from flat couch tops. Therefore, in instances where a flat couch top is preferred, the diagnostic images may be deformed to fit the flat couch top such that a separate radiotherapy simulation is not needed. The system and methods provided herein address the use of couches of various shapes in radiotherapy treatment planning and treatment, including the flat and curved couch tops, while eliminating a radiotherapy simulation scan. For example, the system and methods provided herein provision the use of diagnostic images with couch tops of any shape for radiotherapy planning without the need for special radiotherapy simulation imaging.

In an embodiment, the system and methods provided herein may deform patient images obtained with a couch of one set of physical properties (e.g. curvature) based on the physical properties (e.g. curvature) of a couch where subsequent medical procedures (e.g. radiation therapy treatment) will be performed.

In another embodiment, the system and methods provided herein combine a curved radiotherapy couch, a volumetric imaging device, image deformation, online radiotherapy planning, and radiotherapy delivery.

I. Image Deformation Based on Treatment Couch Shape

Figure 1B:
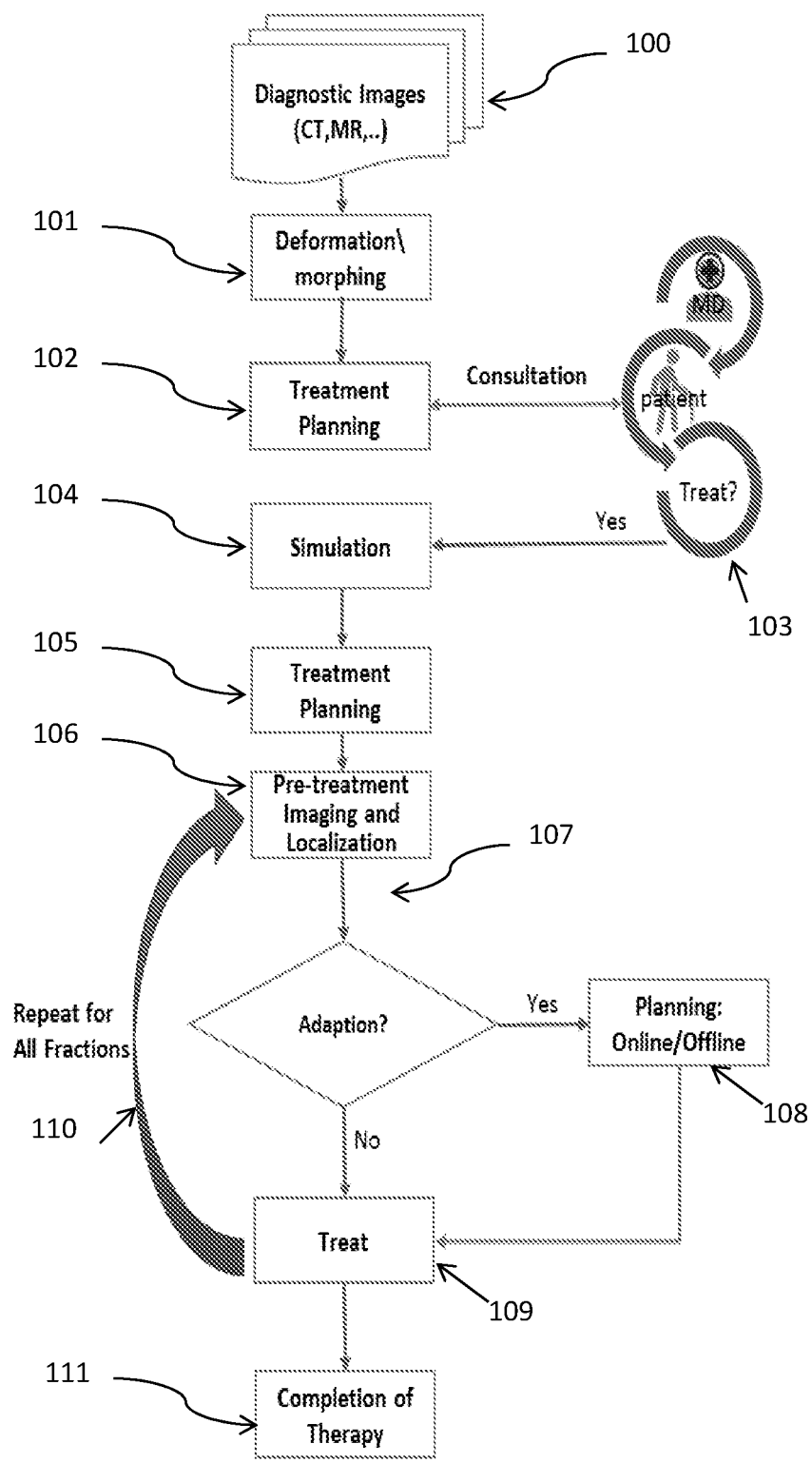
FIG. 1B shows the same radiotherapy method as in FIG. 1A but with an addition of conventional radiotherapy simulation and treatment planning steps.

A description of a method for radiotherapy treatment planning using image deformation based on treatment couch shape, as illustrated in FIG. 1A, is first disclosed herein. A discussion of a method for radiotherapy treatment planning with the addition of conventional radiotherapy simulation and treatment planning steps as illustrated in FIG. 1B will then follow. These variations shall be described herein as the various embodiments are set forth.

The methods shown in FIGS. 1A and 1B are provided by way of example, as there are a variety of ways to carry out the method. Additionally, while the example methods are illustrated with a particular order of blocks, those of ordinary skill in the art will appreciate that FIGS. 1A and 1B and the blocks shown therein can be executed in any order that accomplishes the technical advantages of the present disclosure and can include fewer or more blocks than illustrated. Each block shown in FIGS. 1A and 1B represents one or more processes, methods or subroutines, carried out in the example method.

Figure 2A:
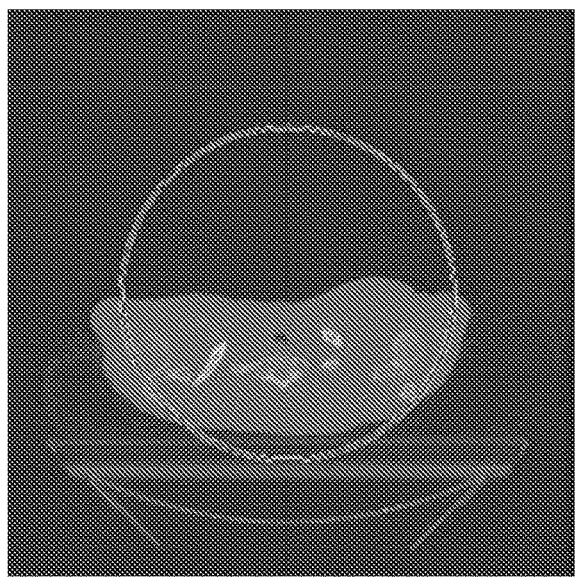
FIG. 2A is an original CT image.
Figure 2B:
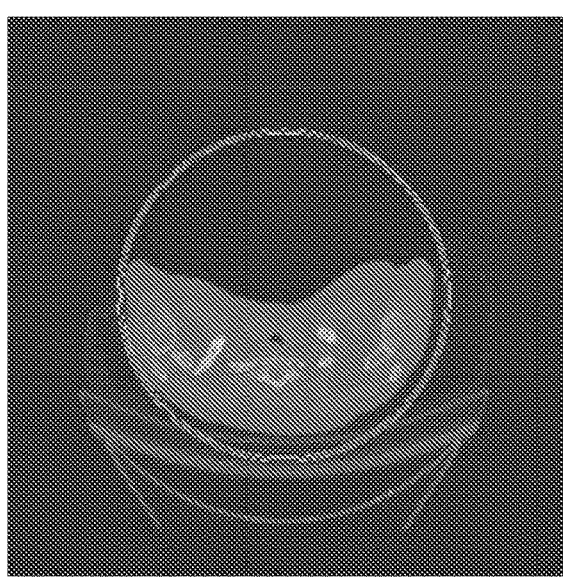
FIG. 2B is the image from FIG. 2A deformed based on couch curvature.

The disclosure now turns to FIG. 1A. FIG. 1A shows the radiotherapy workflow in an embodiment. The method can begin at step 100. Step 100 represents diagnostic images from workup studies or other images available for the patient. These images do not have to be of the same modality and there is no practical limit on how many data sets can be used in this step. Non-limiting examples of diagnostic images include CT images, MR images, PET images, or any other diagnostic image. In step 101, diagnostic\workup images selected from step 100 are deformed based on the geometric properties of couch shape of the treatment machine. In this step, patient images acquired on an imaging system with a couch with one set of physical properties (e.g. curvature) are morphed/deformed based on the physical properties (e.g. curvature) of the treatment machine couch. FIG. 2A shows images acquired with a CT scanner equipped with a flat table top and FIG. 2B shows this image deformed based on a couch with a curved table top. There are many morphing/deformation methods known in the art that can be used in step 101. In one embodiment, a biomechanical deformation model can be used for this step. Here, to model the change of patient anatomy from a couch with one set of physical properties (e.g. curvature) to a couch with another set of physical properties (e.g. curvature), a patient image is divided into a number of small voxels. The large deformation is accumulated on a number of much smaller displacement along the normal of the couch tops with known boundary conditions such as curvature of the couch top. Yet in another embodiment, Artificial Intelligence can be used in step 101. Here, for any new patient, an algorithm, based on either deep machine learning or similarity checks such as cross correlation, dice coefficient and mutual information, finds a good match in the database in terms of anatomy, diagnosis and tumor location. Subtle change between the diagnostic scan of the new patient and the diagnostic scan of the matched patient from the database are calculated through deformable image registration. The simulated scan of the matched patient is used as the primary image for the new patient while fine adjustment based on the subtle change obtained on diagnostic images is also applied.

Figure 3A:
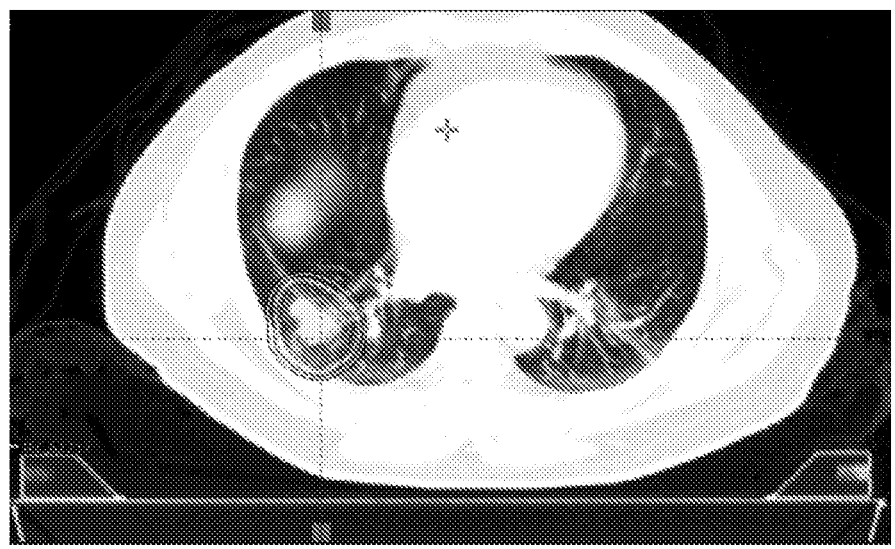
FIGS. 3A, 3B, and 3C show a radiotherapy treatment plan created on an original CT image.
Figure 3B:
Figure 3C:
Figure 4A:
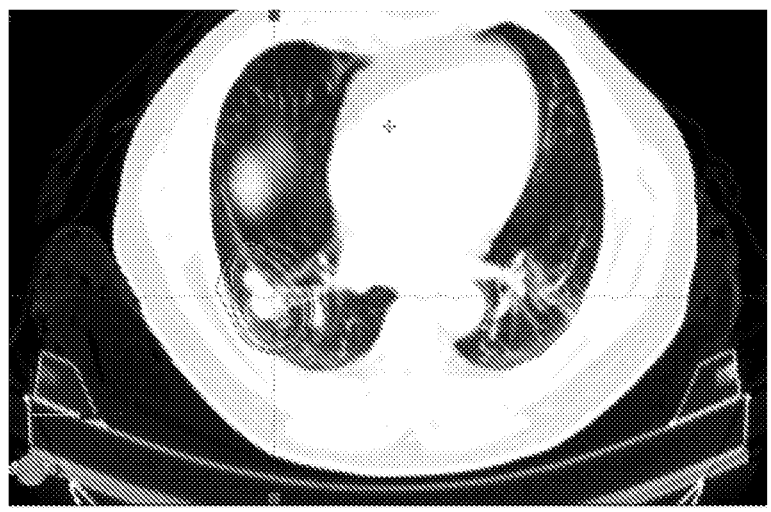
FIGS. 4A, 4B, and 4C show a radiotherapy treatment plan created on a deformed/morphed CT images based on flat couch top.
Figure 4B:
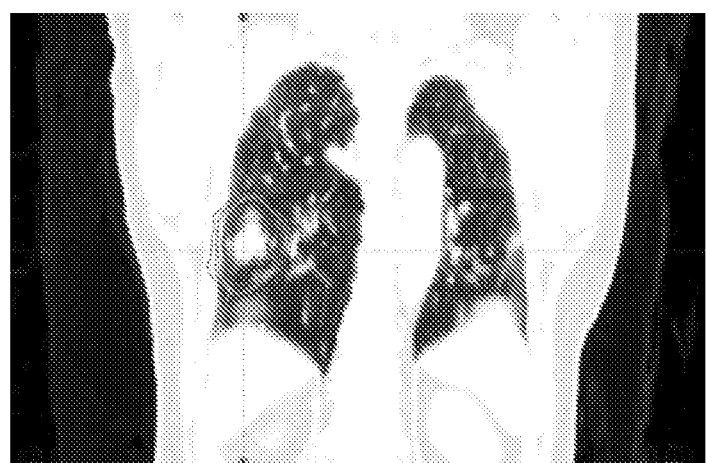
Figure 4C:
Figure 5:
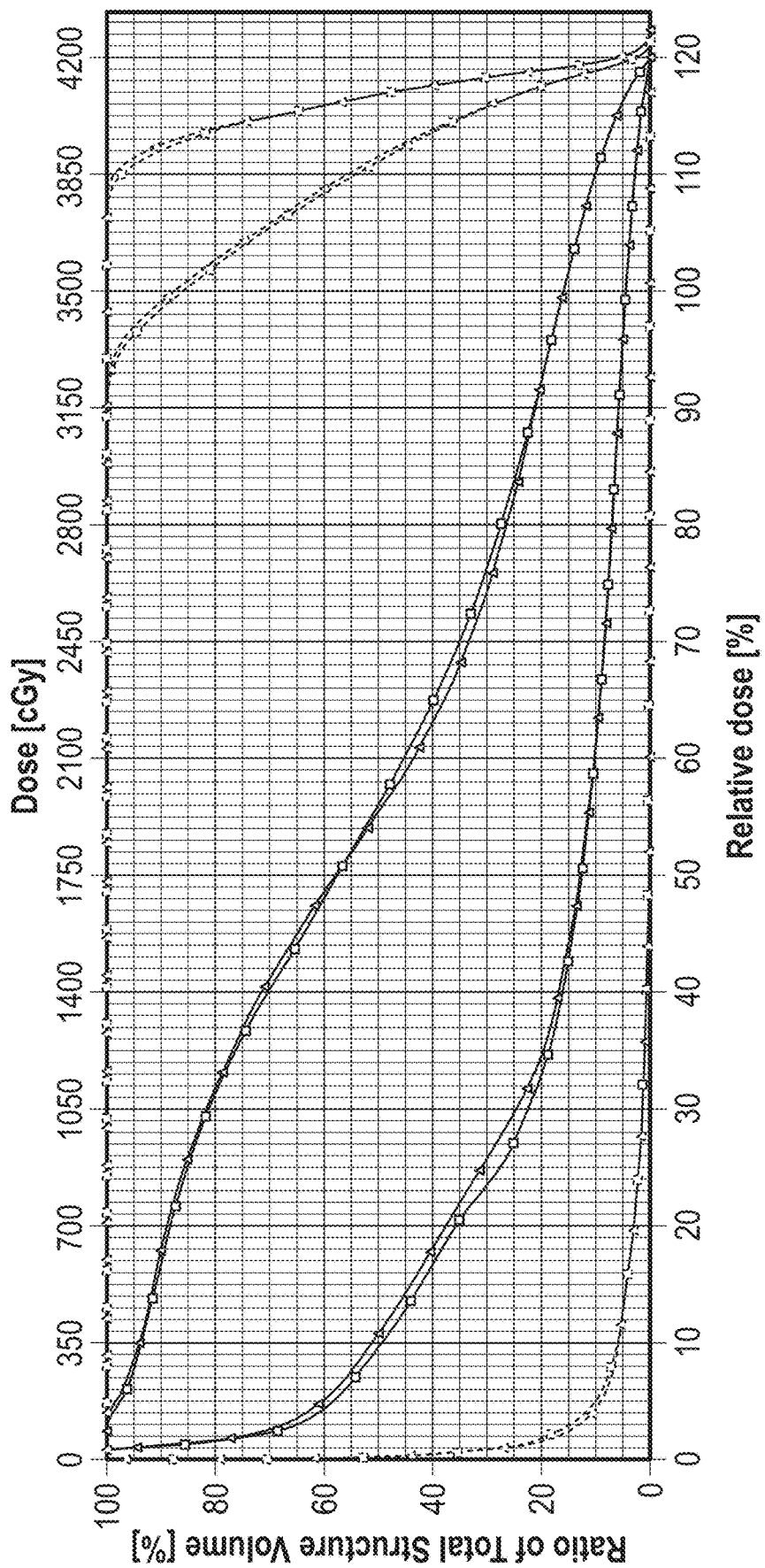
FIG. 5 is comparison of dose volume histograms (DVHs) for a plan originally made on diagnostic image with curved ouch (from FIGS. 3A-3C) and a plan adapted from the original plan on deformed/morphed CT image based on flat couch (FIGS. 4A-4C).
Figure 6:
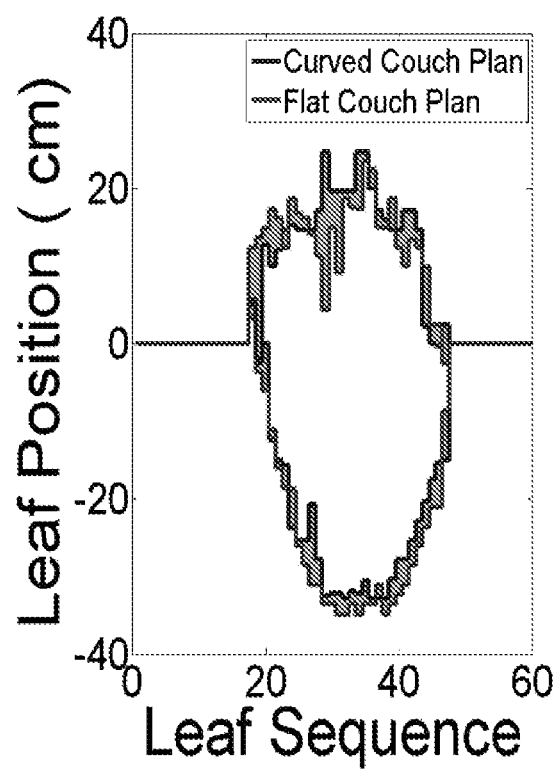
FIG. 6 shows an outline of the same radiotherapy beam from the two plans from FIGS. 4A-4C and 5A-5C. Difference (highlighted in green) in one of the treatment portals at the same gantry angle is insignificant.

In step 102, images deformed in step 101 are used to create a radiotherapy treatment plan. The radiotherapy plan can employ any radiation modality and any method of radiation delivery. Non-limiting examples of radiation modalities include photons, electrons, and protons. Non-limiting examples of radiation delivery include fixed opened beams, intensity modulated radiation therapy, and arc based delivery techniques. The shape of the couch should not have an impact on the quality of radiotherapy treatment plans where it would preclude patient from treatment. In an embodiment, diagnostic images can be first deformed and then a treatment plan created. In another embodiment, a treatment plan can be first created and then the diagnostic images and doses can be deformed. FIGS. 3A-3C show a treatment plan created on anatomy with a flat couch top. FIGS. 4A-4C show a treatment plan created anatomy deformed to a curved couch top. The DVH comparison in FIG. 5 shows minimal differences between the two plans. FIG. 6 shows outlines of the same radiotherapy beam from the two plans and the minimal changes in the shape of the beam. FIGS. 3A-6 demonstrate that, if desired, steps 101 and 102 could be reversed. A plan made using a diagnostic image with curved couch can be easily adapted to plan acceptable for treatment with flat couch.

In step 103, the treatment plan created in step 102 is used between the healthcare providers (e.g. physicians) and\or healthcare providers and the patient to decide on the course of the therapy. The availability of a treatment plan at this stage in the treatment planning process makes decision making more informed.

Once the treatment decision is reached, a patient can go directly to treatment in step 106. Alternatively, patient could go through conventional radiotherapy simulation and treatment planning process, as seen in FIG. 1B in steps 104 and 105, respectively. The treatment plan created in step 102 can be used to inform and guide treatment imaging in step 104 and treatment planning in step 105. The flow of steps 106 through 111 is an exemplary embodiment and any combination of these steps and omission of some steps can achieve patient treatment. It should be also noted that the radiotherapy system used for patient treatment can be any external beam radiotherapy system. The radiotherapy system and may include, but is not limited to a C-shape linear accelerator, an O-shape linear accelerator, a proton machine, a machine with electron beams, a MR-linac, or a linear accelerator with a separate computed tomography scanner, etc. This non-exhaustive list of radiotherapy machines which can be used in this part of patient treatment demonstrates that the present invention is compatible with any external beam radiotherapy machine. In step 106, the patient is imaged and the patient's position and\or couch position are optionally adjusted to place the patient closer to the desired treatment position. If the treatment delivery system is accompanied with an ability to modify the treatment plan (adaptation) based on the images acquired on the treatment machine, this may be accomplished through steps 107 and 108 if there is a need for plan modification. Otherwise, once the desired patient position is achieved in step 106 and/or an adaptive plan is created, the patient may be treated in step 109. Steps 107 and 108 are optional and can include on-line adaption. Other embodiments may include processes where the treatment plan is adjusted off-line prior to the patient's next treatment. The treatment process in steps 106 through 109 may be repeated for as many times (fractions) as prescribed for the patient treatment. The combination of steps 106 through 109 and which steps are performed may depend on patient's daily anatomy and other decisions but not all of the steps would need to be performed for each fraction. In one embodiment, the method for radiotherapy treatment planning may include the steps 101, 102, and 103 and deforming patient images obtained with a couch of one set of physical properties (e.g. curvature) based on the physical properties (e.g. curvature) of a couch where subsequent medical procedures (e.g. Radiation therapy treatment) will be performed.

Figure 12:
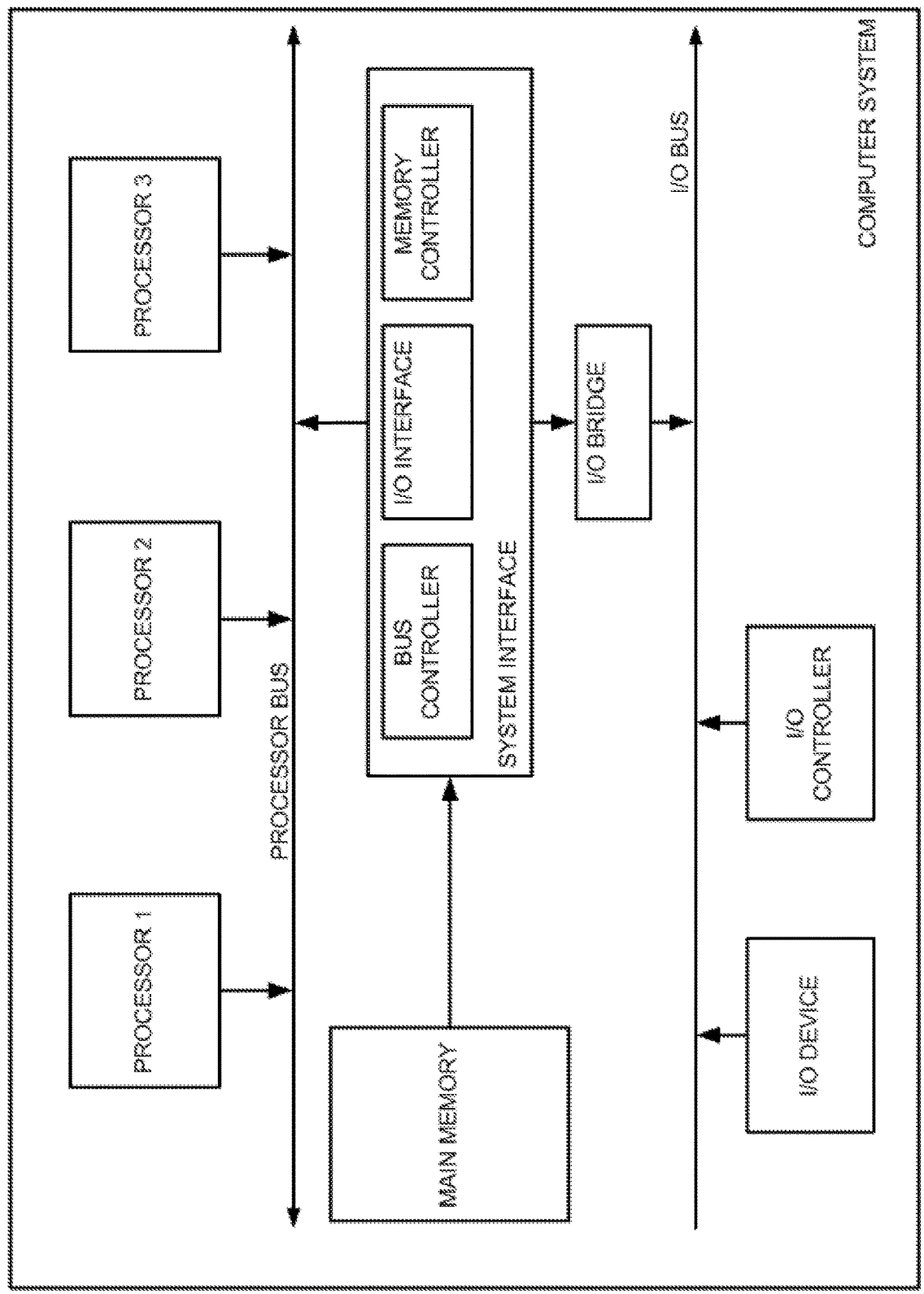
FIG. 12 is a diagram illustrating an example of a computing system which may be used in implementing various embodiments of the present disclosure.

FIG. 12 is a block diagram illustrating an example of a computing device or computer system which may be used in implementing the embodiments disclosed above. The computer system (system) includes one or more processors. The processors may include one or more internal levels of cache (not shown) and a bus controller or bus interface unit to direct interaction with the processor bus. The processor bus, also known as the host bus or the front side bus, may be used to couple the processors with the system interface. The system interface may be connected to the processor bus or to interface other components of the system with the processor bus. For example, the system interface may include a memory controller for interfacing a main memory with the processor bus. The main memory typically includes one or more memory cards and a control circuit (not shown). The system interface may also include an input/output (I/O) interface to interface one or more I/O bridges or I/O devices with the processor bus. One or more I/O controllers and/or I/O devices may be connected with the I/O bus, such as the I/O controller and I/O device as illustrated.

The I/O device may also include an input device (not shown), such as an alphanumeric input device, including alphanumeric and other keys for communicating information and/or command selections to the processors. Another type of user input device includes cursor control, such as a mouse, a trackball, or cursor direction keys for communicating direction information and command selections to the processors and for controlling cursor movement on the display device.

The system may include a dynamic storage device, referred to as main memory, or a random access memory (RAM) or other computer-readable devices coupled to the processor bus for storing information and instructions to be executed by the processors. Main memory also may be used for storing temporary variables or other intermediate information during execution of instructions by the processors. The system may include a read only memory (ROM) and/or other static storage device coupled to the processor bus for storing static information and instructions for the processors.

The system set forth in FIG. 12 is but one possible example of a computer system that may employ or be configured in accordance with aspects of the present disclosure.

According to one embodiment, the above techniques may be performed by the computer system in response to the processor executing one or more sequences of one or more instructions contained in main memory. These instructions may be read into main memory from another machine-readable medium, such as a storage device. Execution of the sequences of instructions contained in main memory may cause processors to perform the process steps described herein. In alternative embodiments, circuitry, such as application specific integrated circuits (ASICs), may be used in place of or in combination with the software instructions. Thus, embodiments of the present disclosure may include both hardware and software components.

A machine readable medium includes any mechanism for storing or transmitting information in a form (e.g., software, processing application) readable by a machine (e.g., a computer). Such media may take the form of, but is not limited to, non-volatile media and volatile media. Non-volatile media includes optical or magnetic disks. Volatile media includes dynamic memory, such as main memory. Common forms of machine-readable medium may include, but is not limited to, magnetic storage medium (e.g., floppy diskette); optical storage medium (e.g., CD-ROM); magneto-optical storage medium; read only memory (ROM); random access memory (RAM); erasable programmable memory (e.g., EPROM and EEPROM); flash memory; or other types of medium suitable for storing electronic instructions.

II. Non-Flat Table Tops in Radiotherapy Systems

Figure 7:
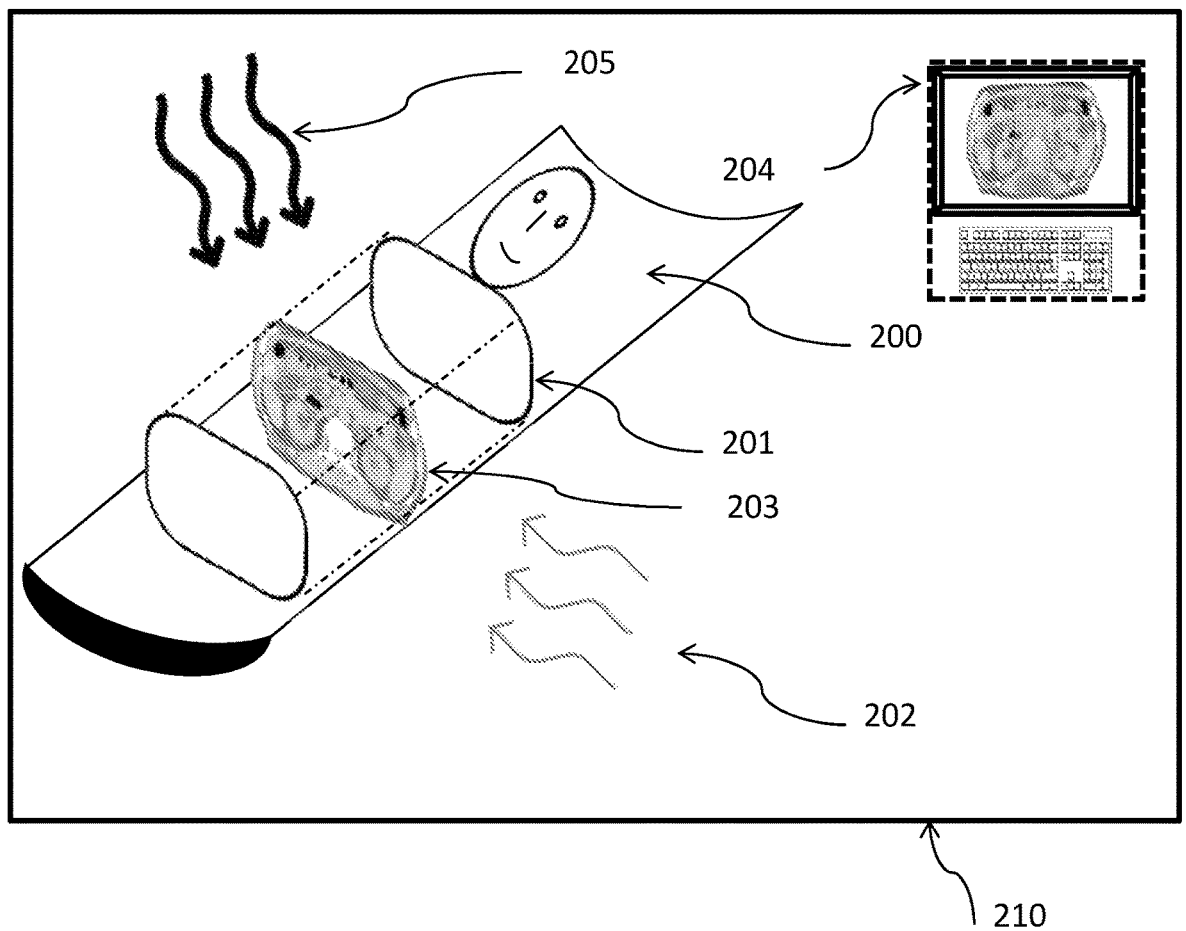
FIG. 7 is a diagram showing the main components of a radiotherapy system with a curved couch, in one embodiment.

FIG. 7 shows components of a radiotherapy delivery system 210 in one embodiment. The radiotherapy delivery system 210 may include a non-flat couch top 200, an imaging component 202, a processor with a treatment planning software component 204, and a therapeutic treatment beam delivery component 205. In this embodiment, a couch with a non-flat top 200 supports a radiotherapy patient 201, the imaging component 202 acquires volumetric images 203 of the patient 201, the treatment planning software 204 uses volumetric images 203 to create a treatment plan for instructions for delivery of the therapeutic treatment beam 205. The imaging component 202 can be any imaging modality which generates volumetric images of a patient. A non-exhaustive list of examples includes kV and/or MV computed tomography imaging, magnetic resonance imaging, ultrasound imaging, multi-angle planar x-ray imaging, optical surface imaging, mm-wave imaging, positron emission computed tomography imaging, etc. The treatment planning software 204 component can be integrated with the radiotherapy delivery system 210 or can be a standalone system which can use volumetric images 203 to create a treatment plan for instructions for delivery of the therapeutic treatment beam 205. When integrated with the radiotherapy device, the treatment planning software 204 component can be an integral part of the control software of the system or a peripheral module enabled through manufacturer provided connection or through an interface for third party software. One example of such interface would be Application Programming Interface (API). The treatment planning software 204 is capable of calculating radiation dose distributions delivered to the patient 201. The treatment planning software 204 can be capable of deformable image registration where images of the patient 201 acquired at some earlier point in time can be registered with volumetric images 203 to determine relative positioning of the non-flat couch top 200 and the therapeutic treatment beam 205. The deformed images do not all need to be of the same modality (CT, MR, PET, etc.) and the treatment planning software can support use and deformation of multimodality images as necessary and/or as available. The treatment planning software 204 can be capable of both, calculating radiation dose distributions delivered to the patient 201 and of deformable image registration where images of the patient 201 acquired at some earlier point in time can be registered with volumetric images 203 to determine relative positioning of the non-flat couch top 200 and the therapeutic treatment beam 205.

Figure 8:
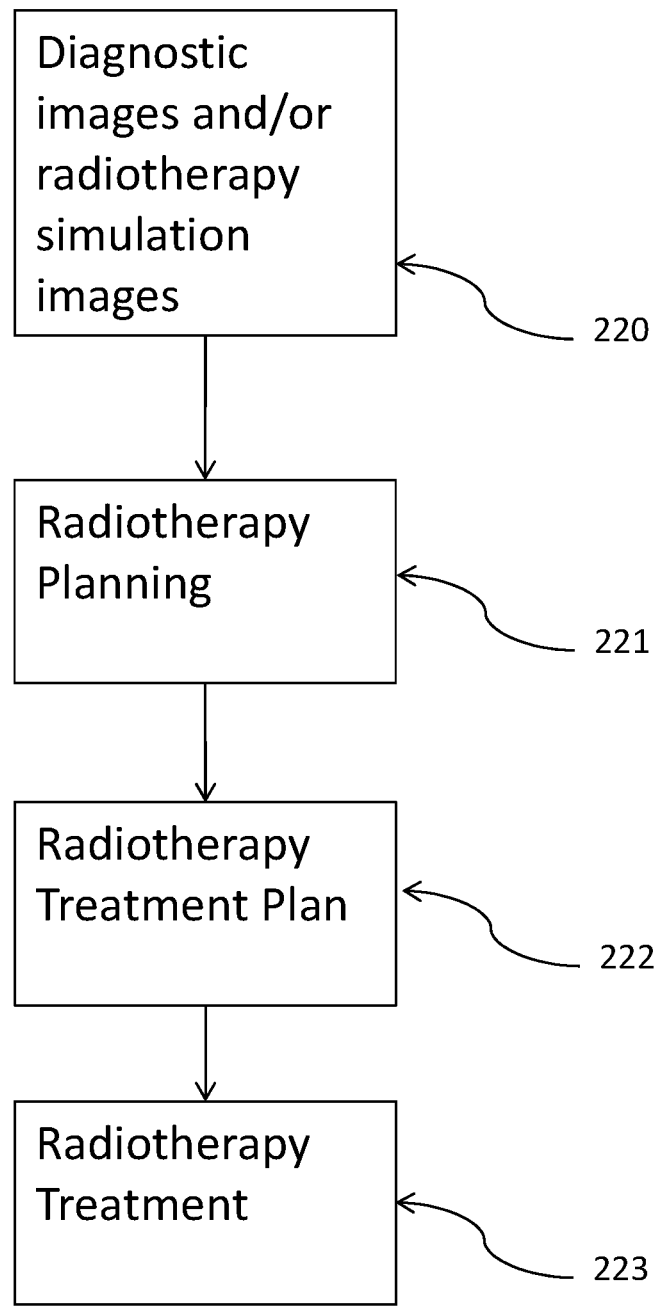
FIG. 8 is a flowchart showing a portion of patient's radiotherapy planning process with a radiotherapy machine with a curved couch, according to one embodiment.

FIG. 8 shows a method of treatment with the embodiment of the radiotherapy delivery system shown in FIG. 7. In this process, patient volumetric images acquired for diagnosis or staging of diseases 220 or radiotherapy simulation images 220 are used in radiotherapy planning process 221 to create a radiotherapy treatment plan 222 for radiotherapy treatment delivery 223 with the radiotherapy delivery system 210 shown in FIG. 7. The radiotherapy planning process includes potentially all steps involved in management of radiotherapy patient, including tumor boards, patient consultation, decisions to treat, selection of therapy options, creation of radiotherapy beam information for use on the treatment machine, etc. The software used in the radiotherapy planning process 221 can be the same treatment planning software 204 as shown in FIG. 7 or completely different software capable of generating a treatment plan with instructions for use with the radiotherapy delivery system 210. The software can also be a collection of different software packages, all used for processing of patient information in preparation for treatment. In such case, these different software packages can still be considered together as treatment planning software 204. The software alternatively can include features to assist healthcare providers, like physicians, in selecting options for patient treatment and management. The present invention, as illustrated in this embodiment, enables the treatment delivery system 210 to consume images and treatment plans from any combination of volumetric imaging devices and treatment planning systems. This enablement is provided through use of a curved couch which should minimize the difference in patient positioning between the planning scan and treatment position and combination of the couch top with therapeutic treatment beam, volumetric imaging, and treatment planning software. Similarly, it should be noted that steps 220, 221, and 222 are optional and that patient's condition can be evaluated directly with volumetric images 203 obtained with the treatment system and treatment planning software 204 can prepare a treatment plan for delivery with the therapeutic treatment beam 205.

Figure 9:
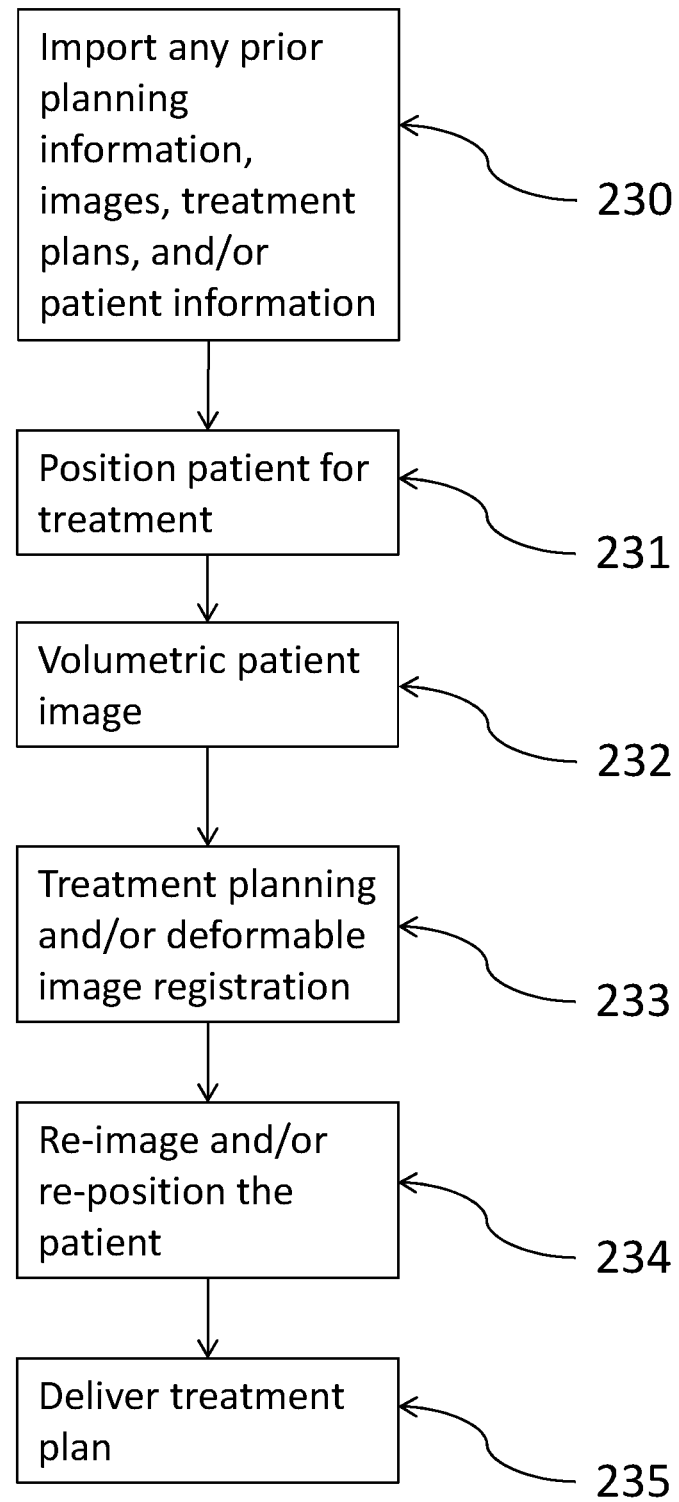
FIG. 9 is a flowchart showing expanded steps of element 223 from FIG. 8.

FIG. 9 shows a more detail description of the step 223 from FIG. 8. In step 230, patient information available from diagnosis and staging and treatment planning, including prior patient images and corresponding radiotherapy treatment plans are imported for use with the radiotherapy delivery system 210. The radiotherapy treatment plan information can range from information describing the intent to treat and potentially a treatment prescription to a full set of machine settings for radiation delivery. It is worth noting that radiotherapy machines equipped with radiotherapy dose calculation capabilities require as little information as components of patient personal information to full radiotherapy treatment information available through Digital Imaging and Communications in Medicine (DICOM) radiotherapy standards (DICOM-RT). Some radiotherapy systems use proprietary radiotherapy plan and delivery information formats. For the purposes of present information, use of data compliant with DICOM-RT standard or data in proprietary formats does not make a difference and in certain situations use of data in proprietary formats can improve efficiency and capabilities of the radiotherapy delivery system 210. In step 231, patient 201 is placed on treatment table 200 in a position for treatment. The position for treatment can be the same as was used for prior patient imaging during diagnostic or radiotherapy simulation imaging or can be a new position more conducive to patient treatment. Similarly, patient positioning can be aided with immobilization devices like body molds, face masks, breast boards, belly boards, wing boards, etc. As the radiotherapy delivery system 210 contains imaging 202 and planning capabilities 204, the system can accommodate changes in patient positioning and/or use of different immobilization devices. In step 232, volumetric imaging system 202 is used to optionally acquire images of patient 201 for purposes of patient positioning and/or creating a radiotherapy treatment plan. In step 233, patient images 203 can be used to create a new treatment plan based on patient's anatomy of the day, adapt an existing treatment plan to the anatomy of the day, select from a library of available treatment plans, perform deformable image registration, determine patient and/or treatment table position for treatment, and/or make other decisions about patient treatment. Radiotherapy treatment planning is a diverse and complex process and the examples provided above are a non-exhaustive list of uses of patient images 203 in the treatment planning and guidance step 233. The outcomes of step 233 may require additional imaging and/or repositioning of patient 201 in step 234. The additional imaging and/or repositioning of patient 201 in the step 234 may also be due to any potential movement and/or changes in patient 201 anatomy during the performance of step 233. In some cases, patient imaging in step 234 is performed as an additional verification that patient has not moved or has not had significant changes in anatomy which would require additional planning or patient positioning. Once an acceptable patient position and treatment plan are obtained and\or verified in step 234, treatment delivery is initiated in step 235. Alternatively, if unacceptable changes in patient position and/or anatomy are seen during the step 234, the process can go back to step 233 and the process in steps 233 and/or step 234 can be repeated as needed until acceptable results are obtained to proceed to patient treatment step 235. The purpose of using curved couch is to reduce the odds going back to step 233.

Figure 10A:
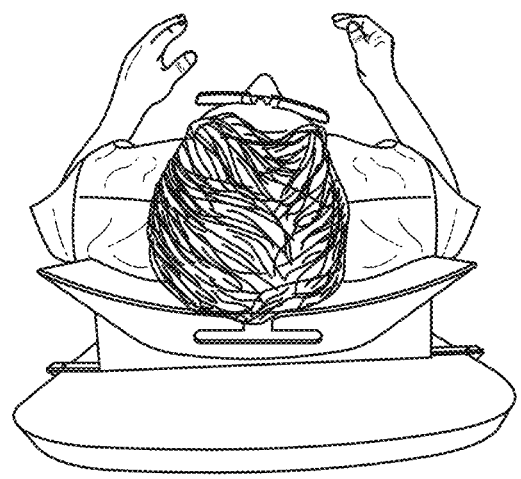
FIG. 10A shows a curved couch mounted on a radiotherapy delivery system and a volunteer positioned on the couch in one embodiment.
Figure 10B:
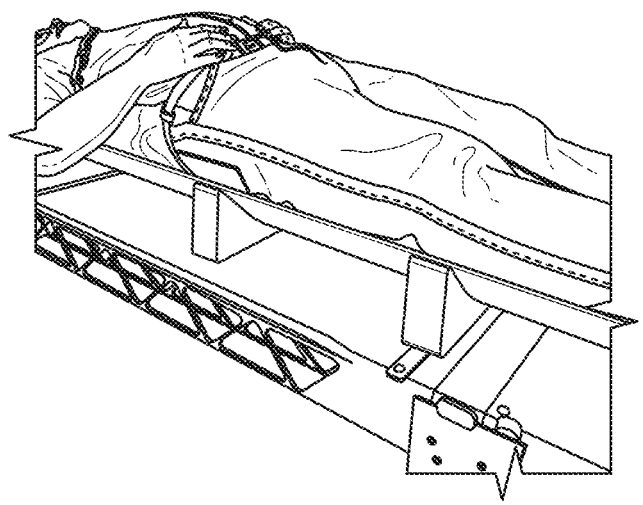
FIG. 10B shows a curved couch mounted on a radiotherapy delivery system and a volunteer positioned on the couch in one embodiment.

In an embodiment, the non-flat couch top is a curved couch top. FIGS. 10A and 10B show an example curved couch with $1/30$ cm$^{-1}$ in curvature mounted on a radiotherapy delivery system and a volunteer positioned on the couch. In an embodiment, the curved couch top that can be used in radiotherapy may have a range of curvature between 0 and $1/10$ cm$^{-1}$.

It will be recognized by those skilled in the art that there are numerous alternative paths to placing and\or attaching a non-flat couch top or a combination of a flat couch top and a non-flat couch top to a radiotherapy delivery device in order to enable method and system described in FIG. 7.

Figure 11A:
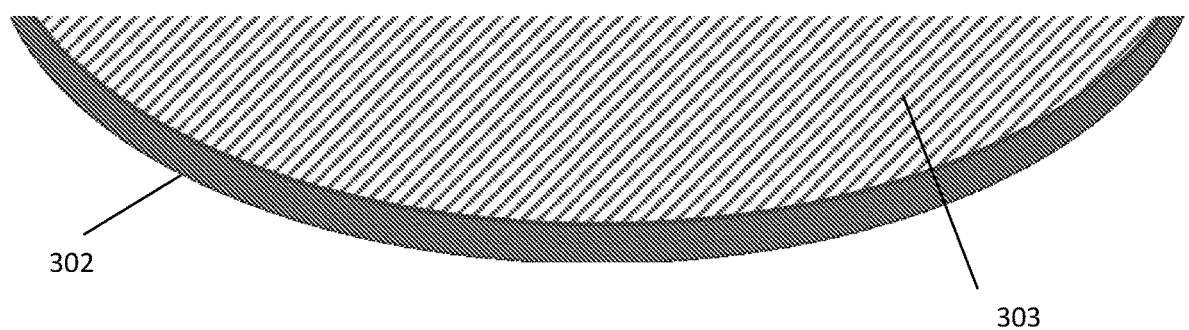
FIG. 11A is a front view of a curved couch top with a flat insert.
Figure 11B:
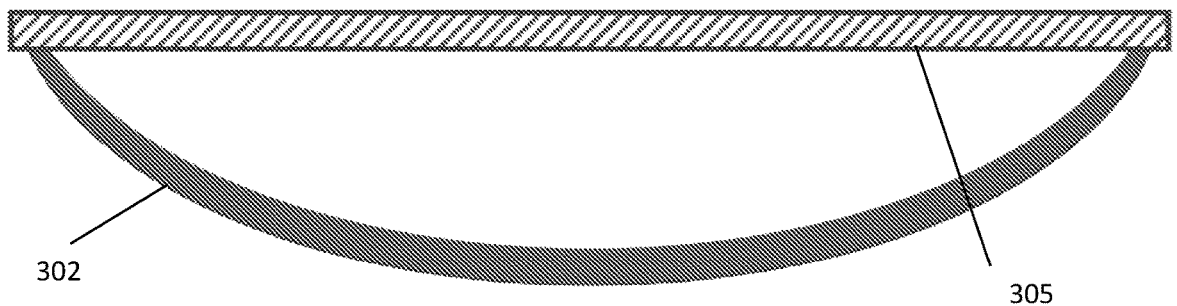
FIG. 11B is a front view of a curved couch top with a flat overlay.

In an embodiment, a flat insert or a flat overlay may be mounted to the non-flat couch top, therefore enabling conversion from a radiotherapy machine with a non-flat couch top to a machine with a flat couch top. In an example, as seen in FIG. 11A, a radiotherapy delivery system with a non-flat couch top 302 may further include a curved insert 303 shaped to fit within the curvature of the non-flat couch top 302 to provide a flat surface on top of the insert 303. In another example, as seen in FIG. 11B, a radiotherapy delivery system with a non-flat couch top 302 may further include a flat overlay 305 with a width larger than the diameter of the curvature of the non-flat couch top 302 to provide a flat surface on top of the insert 303. In these embodiments, the flat couch top may be indexable.

Figure 11C:
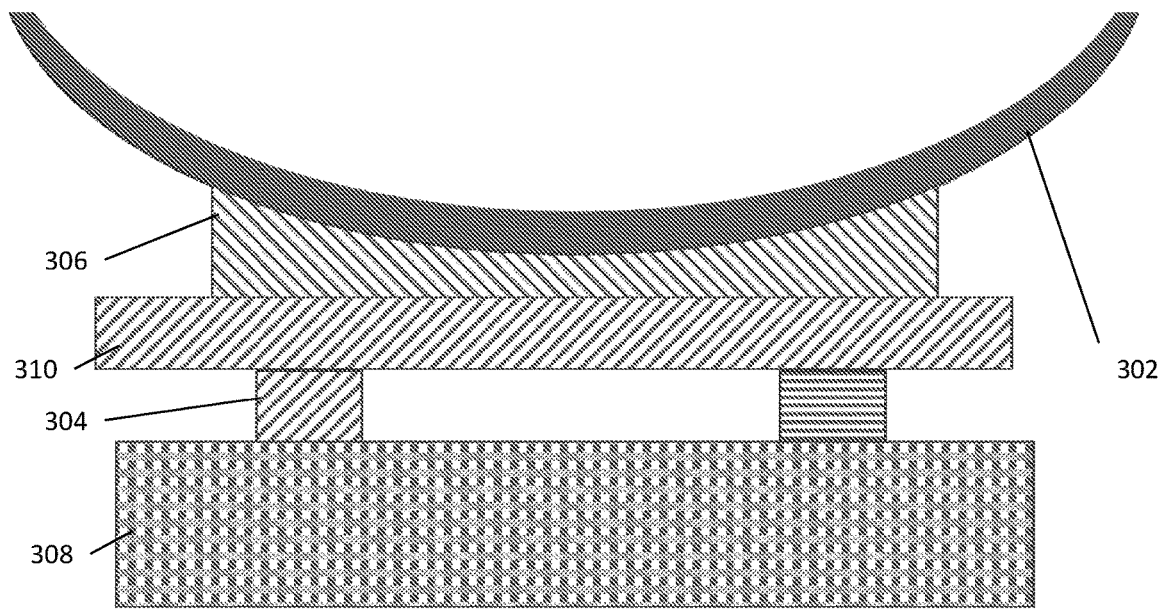
FIG. 11C is a front view of a curved couch top as an overlay on a flat couch top.

In an embodiment, the non-flat couch top 302 is overlayed on top of a flat couch 310, as seen in FIGS. 10A-10B and 11C. The flat couch top 310 may remain attached to the base 308 infrastructure through supporting bars 304 and a curved couch overlay 306 may rest on the surface of the flat couch top 310 and cradle the non-flat couch top 302. The non-flat couch top may be optionally indexed on a flat couch top. This embodiment allows conversion of a conventional flat couch top to a non-flat couch top.

Figure 10C:
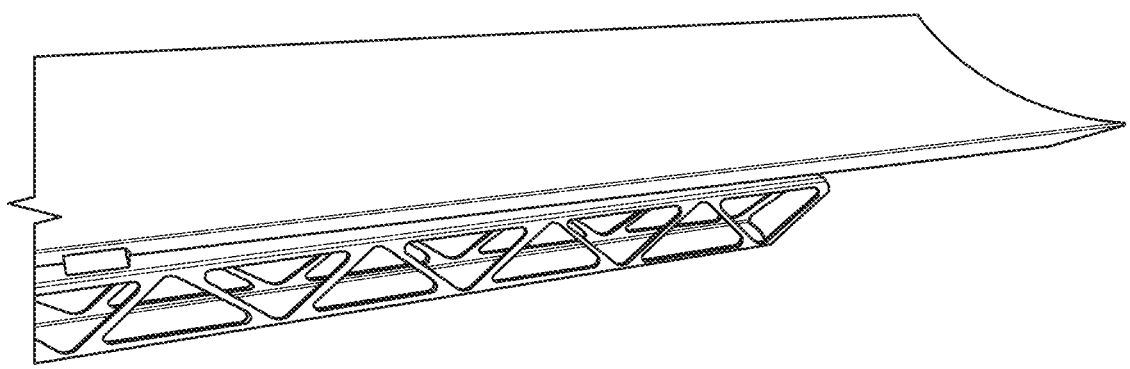
FIG. 10C shows a curved couch top directly mounted on a couch base.
Figure 11D:
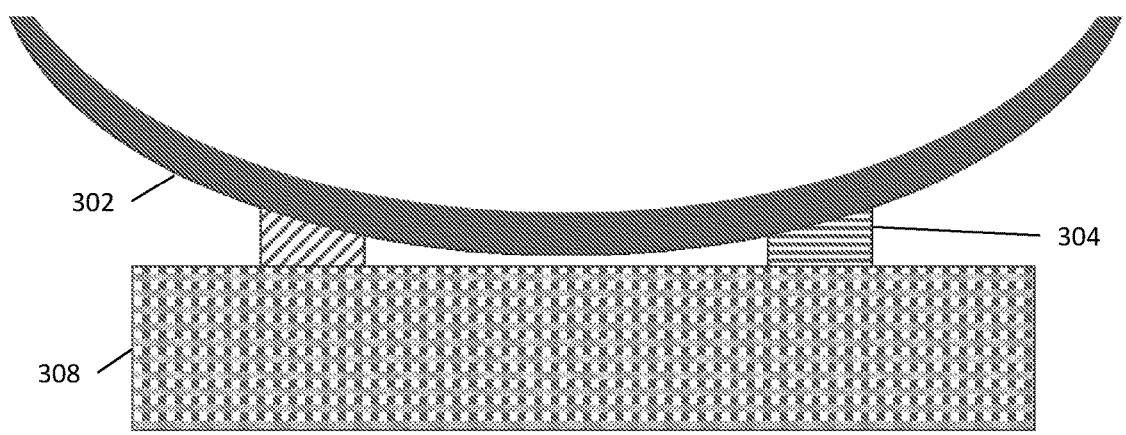
FIG. 11D is a front view of a curved couch top directly mounted on a couch base.

In another embodiment, the non-flat couch top 302 is directly mounted to the base 308 infrastructure of the flat couch, without the flat couch top, as seen in FIGS. 10C and 11D. Supporting bars 304 may be used to assist in mounting the non-flat couch top 302 to the base 308. In this embodiment, the mounting of the couch resembles closer to the mounting of couch as in conventional diagnostic imaging devices (CT, MR, PET, SPECT, etc.).

In an embodiment, the non-flat couch is indexable. For example, the non-flat couch may include notches, holes, or screws to index an immobilization device on the couch. In an embodiment, the non-flat couch may have a width between about 20 cm and about 60 cm. The non-flat couch width may be optimized for each radiotherapy delivery system.

In some embodiments, a curved couch top may aid in immobilization and setup reproducibility. Without being limited to a particular theory, gravity helps with positioning a patient in the middle of a curved couch and can help pull a patient back to the midline of the couch when the patient moves. Improved patient positioning can lead to improved radiation dose distributions. In some embodiments, a curved couch may bring patients closer to a circular center and minimize extensions available for collision.

Having described several variations, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the presently disclosed variations teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

Numerous examples are provided herein to enhance the understanding of the present disclosure. A specific set of statements are provided as follows.

Statement 1: A method for radiotherapy treatment planning comprising: identifying a diagnostic couch top shape of a diagnostic imaging modality; identifying a radiotherapy couch top shape of a radiotherapy system; and deforming at least one diagnostic image of a patient acquired from the diagnostic imaging modality based on the radiotherapy couch top shape.

Statement 2: The method of Statement 1 further comprising: creating a treatment plan for the patient based on the at least one deformed diagnostic image; and bypassing a radiotherapy simulation scan.

Statement 3: The method of Statement 1, wherein deforming the at least one diagnostic image comprises using a biomechanical deformation model.

Statement 4: The method of Statement 1, wherein deforming the at least diagnostic image comprises using artificial intelligence.

Statement 5: The method of Statement 1, wherein the at least one deformed diagnostic image is close to the actual radiotherapy treatment position.

Statement 6: The method of Statement 1, wherein the treatment plan comprises a calculation of a radiation dose distribution on the at least one deformed diagnostic image.

Statement 7: The method of Statement 1, wherein the treatment plan comprises a physician decision plan made in tumor boards, multidisciplinary clinics, patient consultations, or combinations thereof.

Statement 8: The method of Statement 1, wherein the treatment plan created based on the at least one deformed diagnostic image is used as is on the first day of treatment.

Statement 9: The method of Statement 1, wherein the treatment plan created based on the at least one deformed diagnostic image is modified based on an image acquired in a radiotherapy treatment room.

Statement 10: The method of Statement 1, wherein the deforming of the at least one diagnostic image is also based on changes to the patient's position.

Statement 11: The method of Statement 1, wherein the diagnostic imaging modality is selected from the group consisting of CT, MRI, PET, and combinations thereof.

Statement 12: The method of Statement 1, wherein the treatment plan based on the at least one deformed diagnostic image based on the geometry of the treatment machine is adapted at a time of the patient's treatment.

Statement 13: At least one non-transitory computer readable medium storing instructions which when executed by at least one processor, cause the at least one processor to: identify a diagnostic couch top shape of a diagnostic imaging modality; identify a radiotherapy couch top shape of a radiotherapy system; and deform at least one image of a patient acquired from the diagnostic imaging modality based on the radiotherapy couch top shape.

Statement 14: The at least one non-transitory computer readable medium of Statement 13, wherein the instructions which when executed by at least one processor, cause the at least one processor to further: create a treatment plan for the patient based on the at least one deformed diagnostic image; and bypass a radiotherapy simulation scan.

Statement 15: The at least one non-transitory computer readable medium of Statement 13, wherein deforming the at least one diagnostic image comprises using a biomechanical deformation model.

Statement 16: The at least one non-transitory computer readable medium of Statement 13, wherein deforming the at least diagnostic image comprises using artificial intelligence.

Statement 17: The at least one non-transitory computer readable medium of claim 14, wherein the treatment plan comprises a calculation of a radiation dose distribution on the at least one deformed diagnostic image.

Statement 18: A radiotherapy delivery system comprising: a volumetric imaging system for acquiring volumetric images of a patient; a non-flat couch top for positioning the patient; and a processor operable to perform deformable image registration.

Statement 19: The system of Statement 18, wherein the processor further utilizes a treatment plan created with diagnostic images from a diagnostic imaging modality.

Statement 20: The system of Statement 19, wherein the treatment plan is created with diagnostic images from the imaging modality with a couch top that has a similar shape as the non-flat couch top.

Statement 21: The system of Statement 20, wherein the patient's body position does not change by more than 5 cm between the imaging modality couch top and the non-flat couch top.

Statement 22: The system of Statement 19, wherein the treatment plan is created with diagnostic images from the imaging modality with a couch top that has a different shape than the non-flat couch top.

Statement 23: The system of Statement 22, wherein the patient's body position changes position by more than 5 cm.

Statement 24: The system of Statement 19, wherein the treatment plan does not utilize a radiotherapy simulation scan.

Statement 25: The system of Statement 18, wherein the non-flat couch top is curved.

Statement 26: A radiotherapy delivery system comprising: a volumetric imaging system for acquiring volumetric images of a patient; a non-flat couch top for positioning the patient; and a processor operable to utilize a treatment plan and determining a radiation dosage with the volumetric images obtained on the delivery system.

Statement 27: The system of Statement 26, wherein the non-flat couch top is curved.

Statement 28: The system of Statement 26, wherein the processor further utilizes a treatment plan created with images from a diagnostic imaging modality.

Statement 29: The system of Statement 28, wherein the processor utilizes a treatment plan created with deformed images from an imaging modality with a couch top that has a similar shape as the non-flat couch top.

Statement 30: The system of Statement 28, wherein the patient's body position is deformed from the imaging modality couch top to the non-flat couch top.

Statement 31: The system of Statement 26, wherein the processor is further operable to deform at least one of the volumetric images of the patient based on the non-flat couch top shape.

Statement 32: The system of Statement 30, wherein the treatment plan is created with images from the imaging modality with a couch top that has a different shape than the non-flat couch top.

Statement 33: The system of Statement 32, wherein the patient's body position changes position by more than 5 cm.

Statement 34: The system of Statement 26, wherein the treatment plan does not utilize a radiotherapy simulation scan.

Statement 35: The system of Statement 26 further comprising a flat couch top operable to be inserted or overlaid over the non-flat couch top.

Statement 36: A method of treating a patient with radiation therapy comprising: acquiring volumetric images of a patient using a volumetric imaging system; positioning the patient on a non-flat couch top of a radiotherapy delivery system; and creating a radiotherapy treatment plan determining a radiation dosage for the patient with the volumetric images.

Statement 37: The method of Statement 36, wherein creating the radiotherapy treatment plan further comprises using images from a diagnostic imaging modality.

Statement 38: The method of Statement 36 further comprising deforming at least one of the volumetric images of the patient based on the non-flat couch top shape.

Statement 39: The method of Statement 36, wherein a flat couch top is inserted or overlaid over the non-flat couch top.

The invention claimed is:

1. A method for radiotherapy treatment planning comprising:
   acquiring at least one diagnostic image of a patient using a diagnostic imaging modality;
   identifying a diagnostic couch top shape of the diagnostic imaging modality;
   identifying a radiotherapy couch top shape of a radiotherapy system; and
   deforming the at least one diagnostic image of the patient acquired from the diagnostic imaging modality based on the radiotherapy couch top shape and the diagnostic couch top shape.

2. The method of claim 1 further comprising:
   creating a treatment plan for the patient based on the at least one deformed diagnostic image; and
   bypassing a radiotherapy simulation scan.

3. The method of claim 2, wherein the treatment plan comprises a calculation of a radiation dose distribution on the at least one deformed diagnostic image.

4. The method of claim 2, wherein the treatment plan comprises a physician decision plan made in tumor boards, multidisciplinary clinics, patient consultations, or combinations thereof.

5. The method of claim 2, wherein the treatment plan created based on the at least one deformed diagnostic image is used as is on a first day of treatment.

6. The method of claim 2, wherein the treatment plan created based on the at least one deformed diagnostic image is modified based on an image acquired in a radiotherapy treatment room.

7. The method of claim 2, wherein the treatment plan based on the at least one deformed diagnostic image is adapted at a time of the patient's treatment based on a geometry of a treatment machine.

8. The method of claim 1, wherein deforming the at least one diagnostic image comprises using a biomechanical deformation model.

9. The method of claim 1, wherein deforming the at least one diagnostic image comprises using artificial intelligence.

10. The method of claim 1, wherein the at least one deformed diagnostic image is close to an actual radiotherapy treatment position.

11. The method of claim 1, wherein deforming the at least one diagnostic image is also based on changes to the patient's position.

12. The method of claim 1, wherein the diagnostic imaging modality is selected from the group consisting of CT, MRI, PET, and combinations thereof.

13. At least one non-transitory computer readable medium storing instructions which when executed by at least one processor, cause the at least one processor to:
   acquire at least one image of a patient using a diagnostic imaging modality;
   identify a diagnostic couch top shape of the diagnostic imaging modality;
   identify a radiotherapy couch top shape of a radiotherapy system; and deform the at least one image of the patient acquired from the diagnostic imaging modality based on the radiotherapy couch top shape and the diagnostic couch top shape.

14. The at least one non-transitory computer readable medium of claim 13, wherein the instructions which when executed by at least one processor, cause the at least one processor to further:
create a treatment plan for the patient based on the at least one deformed image; and
bypass a radiotherapy simulation scan.

15. The at least one non-transitory computer readable medium of claim 14, wherein the treatment plan comprises a calculation of a radiation dose distribution on the at least one deformed image.

16. The at least one non-transitory computer readable medium of claim 13, wherein deforming the at least one image comprises using a deformation model.

17. The at least one non-transitory computer readable medium of claim 13, wherein deforming the at least one image comprises using artificial intelligence.

18. A method of treating a patient with radiation therapy comprising:
acquiring volumetric images of a patient using a volumetric imaging system;
determining a positioning of the patient on a non-flat couch top of a radiotherapy delivery system; and
creating a radiotherapy treatment plan determining a radiation dosage for the patient with the volumetric images, wherein creating the radiotherapy treatment plan comprises using the positioning of the patient on the non-flat couch top of the radiotherapy delivery system.

19. The method of claim 18, wherein creating the radiotherapy treatment plan further comprises using images of the patient from a diagnostic imaging modality.

20. The method of claim 18, further comprising deforming at least one of the volumetric images of the patient based on a shape of the non-flat couch top of the radiotherapy delivery system.

* * * * *